United States Patent [19]

Price et al.

[11] Patent Number: 5,756,098
[45] Date of Patent: May 26, 1998

[54] METHODS FOR THE EXTRACTION OF PHYTOCHEMICALS FROM FIBROUS PLANTS IN THE ABSENCE OF SOLVENT

[75] Inventors: Christopher H. Price, Woodbury; Dale Hedtke, St. Paul, both of Minn.; Geoffrey N. Richards, Missoula, Mont.; Michael S. Tempesta, El Granada, Calif.

[73] Assignees: The University of Montana, Missoula, Mont.; Larex International, Inc., St. Paul; Crown Iron Works Company, Roseville, both of Minn.

[21] Appl. No.: 571,231

[22] Filed: Dec. 12, 1995

[51] Int. Cl.$^6$ .......................... A01N 65/00; A61K 35/78; B30B 13/00; C07G 1/00
[52] U.S. Cl. .................... 424/195.1; 424/196.1; 100/35; 100/37; 100/127; 100/128; 100/145; 366/83; 530/507; 530/501; 530/502; 536/127; 536/103; 536/124; 536/128
[58] Field of Search .................. 424/195.1, 196.1; 100/35, 37, 127, 128, 145; 366/83; 530/507, 501, 502; 536/127, 128, 124, 103

[56] References Cited

U.S. PATENT DOCUMENTS

| | | | |
|---|---|---|---|
| 1,339,489 | 5/1920 | Weiss | 100/35 |
| 1,358,129 | 11/1920 | Weiss | 100/35 |
| 1,861,933 | 6/1932 | Murdock | 100/35 |
| 1,913,607 | 6/1933 | McMillan | 100/35 |
| 2,008,892 | 7/1935 | Asplund | 92/20 |
| 2,047,170 | 7/1936 | Asplund | 92/21 |
| 2,073,616 | 3/1937 | Acree | 127/30 |
| 2,832,765 | 4/1958 | Roberts et al. | 260/209 |
| 3,325,473 | 6/1967 | Herrick et al. | 260/209 |
| 3,337,526 | 8/1967 | Adams | 260/209 |
| 4,357,865 | 11/1982 | Knuth et al. | 100/117 |
| 5,116,969 | 5/1992 | Adams et al. | 536/128 |

OTHER PUBLICATIONS

Adams, M.F. and B.V. Ettling, "Larch Arabinogalactan", *Industrial Gums*, 2d ed., R.L. Whistler and J.N. BeMiller Eds., Academic Press, New York, 415–427 (1973).

Beutler, E., "Red Cell Metabolism", *Methods In Hematology*, 16:Ch. 8, 99–105, Church Livingstone, New York, (1986).

Lowary and Richards, "Analysis Of A Hydroxystilbene Glucoside In Several Softwood Barks", *J. Of Wood Chem. And Tech.*, 9(3):333–339 (1989).

Okubo, et al., "In Vivo Effects Of Tea Polyphenol Intake On Human Intestinal Microflora And Metabolism", *Biosci. Biotech. Biochem.*, 56(4): 588–591 (1992).

*Primary Examiner*—Marian C. Knode
*Assistant Examiner*—Ali R. Salimi
*Attorney, Agent, or Firm*—Arnall Golden & Gregory, LLP

[57] ABSTRACT

Methods and apparatus are provided for the recovery of organic compounds from fibrous plant materials. Organic compounds which can be recovered from the fibrous plant materials include plant metabolites, such as arabinogalactan and phenols, which can be isolated from the wood, for example, of the Western Larch and Tamarack tree varieties. In addition to the recovery of organic compounds from wood, fibrous wood products also may be isolated, in the form of a clean fiber that can be used, for example, as raw material in wood processing applications or in the manufacture of high quality paper products. In one embodiment, a fibrous plant material first is compressed, to recover a liquid exudate and a first pressed plant fiber product. Optionally, the fibrous plant material, such as wood particles, is compressed in the substantial absence of any added solvent, to produce a pure normal liquid exudate and a first pressed plant product. The first plant fiber product then may be impregnated with, for example, an aqueous solvent, to recover an extract liquor and impregnated plant fiber. The impregnated plant fiber then is compressed to recover a liquid pressate and a second pressed fiber product. Using these methods, in one embodiment, a substantially pure arabinogalactan exudate and a wood fiber product can be recovered from wood of the genus Larix, with minimal coextraction of phenols. Additionally, a variety of different plant metabolites may be isolated and/or identified from different kinds of woody plants using the methods and apparatus.

24 Claims, 1 Drawing Sheet

METHODS FOR THE EXTRACTION OF PHYTOCHEMICALS FROM FIBROUS PLANTS IN THE ABSENCE OF SOLVENT

BACKGROUND OF THE INVENTION

The present invention relates generally to the methods of isolating organic compounds from vegetable matter.

Natural plant materials such as wood are a source of many useful organic chemicals. For example, The Yew tree is a source of the pharmaceutical taxol. Additionally, arabinogalactan is a well-known polysaccharide found abundantly in the Larix genus, e.g., Western Larch (*Larix occidentalis*) and Tamarack or Eastern Larch (*Larix laricina*) and in smaller amounts in other trees, such as hemlock, black spruce, douglas fir, cedar, juniper, and sugar maple.

Arabinogalactan is of particular commercial interest because its physical properties are well suited for a variety of applications. Arabinogalactan is a polysaccharide, including galactose and arabinose units in varying ratios, which varies in molecular weight from low molecular weight polymers to large macromolecules. Arabinogalactan is completely soluble in water over a wide range of temperatures, and has good emulsification properties. Arabinogalactan remains soluble even at high concentrations, resulting in stable, low viscosity solutions.

Arabinogalactan is used in a wide range of commercial applications, e.g., in the printing, mining, biological research and food industries. For example, in the food industry, arabinogalactan is commonly used as an emulsifier, stabilizer or binder in oils, sweeteners, dressings, flavorings and puddings. Arabinogalactan is also used as a soluble plant-derived dietary fiber. Arabinogalactan is used as well for mucic acid production, in lithographic solutions, and in photographic development solutions. A review of the use of arabinogalactan gums is discussed in Adams, M. F. and B. V. Ettling, *Industrial Gums*, 2d ed., R. L. Whistler and J. N. BeMiller Eds., Academic Press, New York, 1973, p. 415–427. A more recent use for arabinogalactan is as a biological density gradient. Beutler, E., *Red Cell Metabolism*, Church Livingstone, New York, Ch. 8, 1986, pp. 99–105.

Arabinogalactan is generally present in the wood of trees such as Larch with other organic compounds such as phenols, including polyphenols. Phenols, as defined herein, are molecules which contain one or more phenol moieties, and include flavonoids such as tannins, aromadendrines, anthocyanins, catecholins, catechins and taxifolins, as well as their oligomers and polymers. Although phenols and other soluble organic compounds are considered impurities with respect to obtaining a refined arabinogalactan solution, these compounds may themselves be desirable as products for other applications either by themselves, or in combination with arabinogalactan. For example, flavonoids, e.g., compounds with a phenyl-$C_3$-phenyl structure where the phenyl rings contain one or more hydroxyl functional groups, have been reported to decrease the amount of putrefactive bacteria while increasing the amount of acid-forming bacteria in the human intestine. Okubo, et al., *Biosci. Biotech. Biochem.*, 56(4):588–91 (1992).

Methods have been developed for recovering soluble organics, such as arabinogalactan, from fibrous natural plant materials, such as wood. Generally, arabinogalactan is recovered from Larch by chipping or grinding the wood and extracting it with water or dilute acidic solutions. The rate of recovery of arabinogalactan from Larch chips was reported to be dependent upon the extraction temperature and the size of the chip, while the amount of arabinogalactan recovered was dependent on the amount of arabinogalactan in the wood chip. Adams, M. F. and B. V. Ettling, *Industrial Gums*, 2d ed., R. L. Whistler and J. N. BeMiller, Eds., Academic Press, New York, 1973, p. 415–427.

U.S. Pat. No. 1,339,489 to Weiss discloses pretreating larch wood particles with steam, grinding the wood particles in the presence of recirculating water, separating the fibrous pulp from the water, recirculating the water back through the grinding operation and then recovering the organic products from the recirculated, concentrated liquor. U.S. Pat. No. 1,861,933 to Murdock discloses comminuting wood particles in the presence of an aqueous liquid, contacting the liquid with the defibrated material for a prolonged time, repeating the previous steps one or more times, and concentrating the extracted solution. U.S. Pat. No. 2,832,765 to Roberts et al. discloses combining dry-comminuted wood particles with aqueous solvents in a system of countercurrent extraction cells, where each cell includes phase separators.

U.S. Pat. No. 3,337,526 to Adams discloses a process used commercially and known in the art as the "Libby Process", in reference to the city of Libby, Mont., where arabinogalactan was commercially produced by St. Regis Paper Company. Adams discloses passing finely divided Larch chips through an extensive multiple-stage counterflow system in which additional fresh wood is continuously or periodically introduced to the system. In the process, an aqueous solvent is used at temperatures ranging from just above the freezing point up to approximately 70° C., and process times of approximately one hour are used to obtain an extract containing approximately 10% arabinogalactan. In one embodiment, Adams discloses mixing Larch wood sized to a practical maximum of 10 mesh with sufficient water to raise the moisture content to about 200%, and then compressing the water-saturated, finely divided wood to recover approximately 70% of the water as an extract. Adams further discloses that an additional compressing cycle can be used to recover approximately 70% of the remaining water from the wood. The time for each compressing cycle is approximately 10 minutes.

Methods also have been developed for the recovery of arabinogalactan as a useful co-product of a pulp-making process. For example, U.S. Pat. No. 1,358,129 to Weiss discloses a process where, in addition to obtaining a liquor rich in soluble organic compounds, the fibrous pulp product is used in a chemical pulp-making operation. U.S. Pat. No. 2,073,616 to Acree discloses recovering galactan from comminuted wood particles by immersing the chips in water greater than approximately 32° C. for several hours. Acree further discloses using repeated extraction to obtain various fractions with different organic solubles.

The arabinogalactan extract obtained from the wood of Larch trees may be refined to obtain a highly refined arabinogalactan solution required in some commercial uses. The concentration of arabinogalactan in the solution is generally increased by drying to remove water. Chemical compounds such as phenols and iron-containing compounds are generally separated from the desired arabinogalactan by precipitating them from the extract with MgO, as disclosed in U.S. Pat. No. 3,325,473 to Herrick et al. Further refinement may include, for example, the removal of the microfine particles and molecules with molecular weights in excess of 1,000,000, and the removal of the lower molecular weight monomers, homopolymers and other materials which contribute to the osmolality of the arabinogalactan solution, as disclosed in U.S. Pat No. 5,116,969 to Adams et al.

Wood pulping methods and equipment which produce fibrous wood products, but which do not recover any useful chemicals from the wood, are known in the art. For example, U.S. Pat. No. 1,913,607 to McMillan discloses a thermal chemical pulping process which uses a pressurized sulfide cooking acid and employs a rocking drum system. U.S. Pat. No. 2,008,892 to Asplund discloses a thermomechanical pulping method that includes pretreating the wood particles with steam at high temperatures and pressures, and then mechanically defibrating the chips.

Variations to the pretreatment steps of the Asplund defibrator pulping process are also known. One such variation is disclosed in U.S. Pat. No. 2,047,170 to Asplund, which discloses a pulping method that includes the addition of a sizing substance prior to the defibration. Modern variations to the pretreatment steps of the Asplund defibrator are disclosed in commercial brochures such as those of Sunds Defibrator AB's PREX-Impregnator, which is directed to a pretreatment process that includes pre-steaming the wood particles in a feed bin, using a first plug screw feeder to compress the steamed wood particles and to feed them to an impregnator with a chemical prior to mechanical refining, impregnating the wood fiber product in the impregnator, and using another plug screw feeder to compress the impregnated wood particles and to feed them to a digester for defibration. The pressate from each of the plug screw feeders is discharged to the sewer, typically through a floor drain located underneath the equipment.

Thus, while there are methods available in the art for recovery of organic chemicals from wood, these methods suffer from various deficiencies. For example, the commercialized "Libby Process" for recovering arabinogalactan from Larch is a complex, multiple stage, counter current process, which requires a significant capital investment. Additionally, the prior art methods of recovering arabinogalactan from Larch trees typically require that the trees be finely divided or defibrated prior to recovering arabinogalactan. This adds to process costs, and may render the resulting fibrous wood by-product unsuitable for paper pulping operations. Further, because the prior art processes saturate the wood particles with water to effect the recovery, significant water consumption exists. Finally, since the resulting arabinogalactan extract has relatively low concentrations of arabinogalactan, significant process costs are associated with drying the extracted solution to increase the concentration of arabinogalactan.

It is therefore an object of the present invention to provide methods and apparatus for efficiently and economically recovering organic chemicals from natural plant materials. It is another object to provide methods for simultaneously recovering organic chemicals and useful polysaccharide products from natural fibrous plant materials. It is a further object of the invention to provide methods and apparatus for isolating new metabolites from the wood, bark or leaves a variety of different woody plants.

SUMMARY OF THE INVENTION

Methods and apparatus are provided for the recovery of organic compounds from fibrous plant materials. Organic compounds which can be recovered from the fibrous plant materials include plant metabolites, such as arabinogalactan and phenols, which can be isolated from the wood, for example, of the Western Larch and Tamarack tree varieties. In addition to the recovery of organic compounds from wood, fibrous wood products also may be isolated, in the form of a clean fiber that can be used, for example, as raw material in wood processing applications or in the manufacture of high quality paper products.

In one embodiment, a fibrous plant material first is compressed, to recover a liquid exudate and a first pressed plant fiber product. Optionally, the fibrous plant material, such as wood particles, is compressed in the substantial absence of any added solvent, to produce a pure normal liquid exudate and a first pressed plant product. The first plant fiber product then may be impregnated with, for example, an aqueous solvent, to recover an extract liquor and impregnated plant fiber. The impregnated plant fiber then is compressed to recover a liquid pressate and a second pressed fiber product. Using these methods, in one embodiment, a substantially pure arabinogalactan exudate and a wood fiber product can be recovered from wood of the genus Larix, with minimal coextraction of phenols. Additionally, a variety of phytochemicals including arabinogalactan and polyphenols can be isolated from further extraction or other refinement of the extract liquor, the liquid pressate or the pressed fiber product. The methods and apparatus thus permit a variety of different plant metabolites to be isolated and/or identified from different kinds of woody plants.

DETAILED DESCRIPTION OF THE INVENTION

Figure 1:
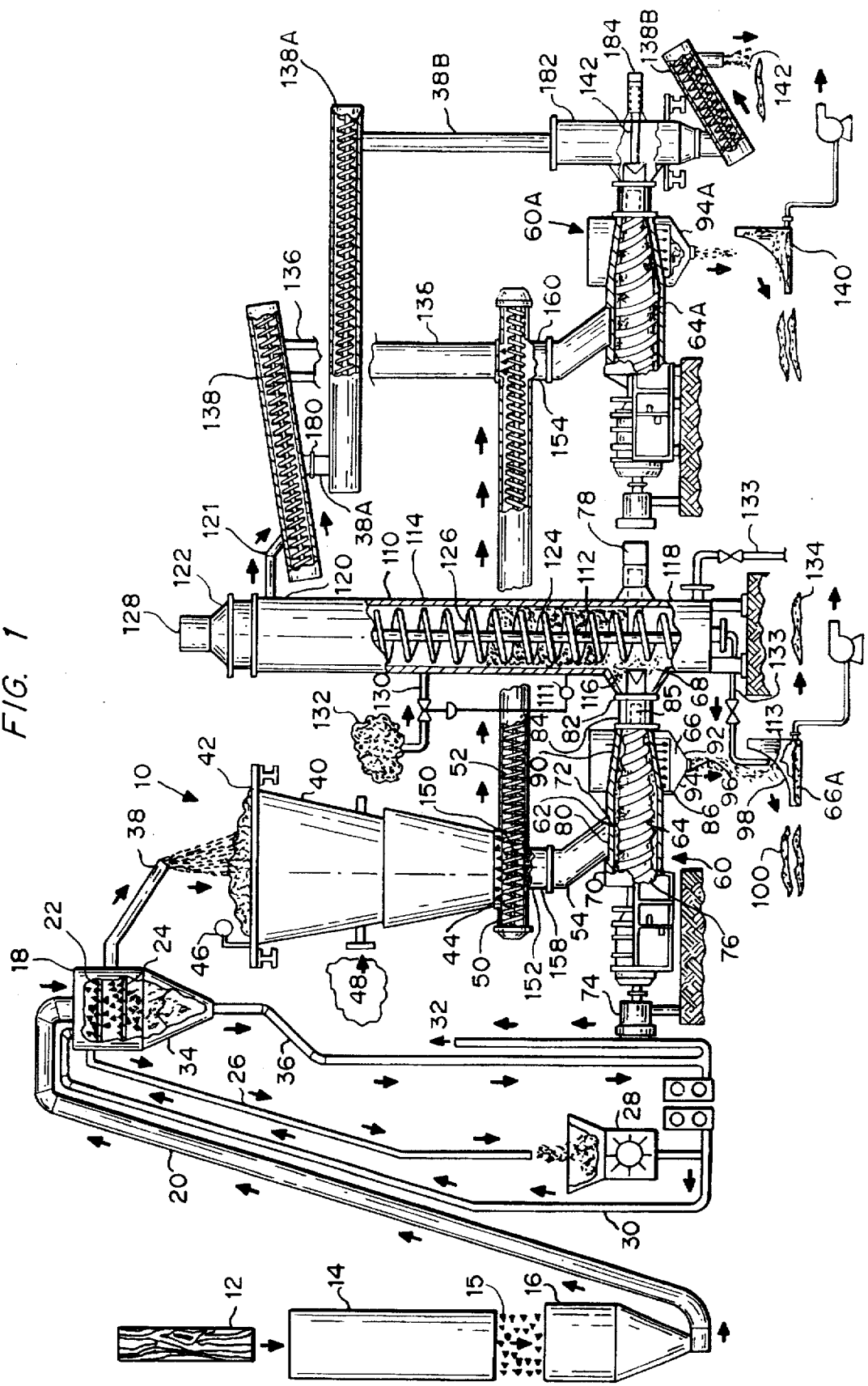
FIG. 1 is a detailed schematic illustration of an equipment configuration suitable to effect the wood chip preparation steps and a single-state, two-stage or bypass process.

Methods and apparatus are provided for the recovery of phytochemicals from vegetable matter. As defined herein the term "phytochemicals" refers to any of a wide range of organic compounds which can be isolated from vegetable matter. Exemplary phytochemicals which can be recovered from the fibrous plant materials include plant metabolites, such as arabinogalactan, and phenols. As defined herein, the term "phenols" includes phenol monomers and polyphenols, and derivatives thereof. Arabinogalactan may be isolated from the wood, for example, of trees of the Larix genus, e.g., Western Larch (*Larix occidentalis*) and Tamarack or Eastern Larch (*Larix laricina*). Exemplary phenols which can be isolated from fibrous plant materials include flavonoids such as tannins, aromadendrines, anthocyanins, catecholins, catechins and taxifolins. In addition to the recovery of organic compounds from wood, fibrous wood products also may be isolated, in the form of a clean fiber that can be used, for example, as raw material in wood processing applications or in the manufacture of high quality paper products.

Fibrous Plant Material

Generally, any fibrous plant material (FPM) may be processed to permit the isolation of a variety of different phytochemicals from the plant material. The particular fibrous plant material is selected based upon the organic compounds to be recovered or upon the characteristics of the fibrous product desired. As defined herein, fibrous plant materials include whole plants and any plant part, including wood, bark, roots, stems, fruits, seeds, petioles, leaves or needles. The plant parts may be derived from trees, plant stalks and other cellulosic materials.

In a preferred embodiment, the fibrous plant material is wood from trees. Examples of trees from which phytochemicals can be isolated include the Yew tree for the recovery of taxol and the Larch tree, for recovery of arabinogalactan. Additionally, phytochemicals can be isolated from the fibrous plant material of other trees such as North American trees, including hemlock, black spruce, douglas fir, cedar, juniper, and sugar maple. For the purpose of illustration, the isolation of phytochemicals from wood of the Larch tree is described herein by way of example, however the methods can be readily be adapted for the isolation of phytochemicals from other fibrous plant materials such as other types of trees. The fibrous plant material and the process steps are selected and designed based on the phytochemical(s) to be recovered or upon the characteristics of the fibrous wood product desired. For recovery of arabinogalactan, wood particles from trees of the genus Larix are the preferred fibrous plant material. The Western Larch tree is particularly preferred.

Processing of Plant Materials

Any of a variety of plant materials can be processed, to refine and recover a preselected phytochemical, or to identify and isolate new phytochemicals, using the methods and apparatus disclosed herein. The choice of fibrous plant material to be processed will depend on the phytochemical to be recovered. Prior to processing, the fibrous plant material, such as wood or bark, for example derived from a tree of the Larix genus, optionally may be sized to a preferred dimension using methods available in the art.

In one embodiment, a fibrous plant material is processed by compressing the plant material in a plug screw feeder extractor to produce a liquid exudate and a pressed plant product. Optionally, the fibrous plant material is compressed in the plug screw feeder extractor in the absence of any added solvent to the fibrous plant material. This permits the recovery of a pure normal liquid exudate and a pressed plant product, which optionally can be further refined to isolate the phytochemical.

Additionally, to isolate phytochemicals from plants, the fibrous plant material may be compressed, preferably with a plug screw feeder extractor, to recover a liquid exudate and a first pressed plant fiber product, and then the first plant fiber product may be impregnated, for example, in an impregnator, with a solvent, thereby to recover an extract liquor and impregnated plant fiber. Optionally, the impregnated plant fiber then may be compressed again, preferably in a plug screw feeder extractor, to recover a liquid pressate and a second pressed fiber product. The fractions obtained during processing, such as the exudate, the liquid pressate, and the second pressed fiber product, can optionally be further refined to recover the phytochemical, for example, by extraction with water or an organic solvent, or by chromatography or centrifuging or other methods available in the art.

Ambient Moisture Content

In one embodiment, the fibrous plant material is compressed in a plug screw feeder extractor in the substantial absence of any added solvent to the fibrous plant material, to recover a pure normal liquid exudate and a first pressed plant fiber product. Thus, the fibrous material has an ambient moisture content, substantially without added solvent. As defined herein, fibrous plant material with an "ambient moisture content" refers to fibrous plant material to which essentially no moisture, in the form of solvents such as water, is added prior to processing. The moisture content may vary depending on different conditions such as the type of fibrous plant material and environmental conditions. The fibrous plant material thus may have a sufficient amount of ambient moisture to enable the recovery of the desired organic chemical without the necessity of adding any solvent to the fibrous plant material.

For the recovery of arabinogalactan from Larch trees, prior to compressing the initial wood material, the wood is preferably at ambient moisture content. As defined herein, ambient moisture content is in the range of about 15–75% moisture (water), and preferably about 50%, on a dry wood basis. This method is preferred for fibrous plant materials of wood or bark of a tree of the genus Larix, since this process produces an exudate including substantially pure arabinogalactan. In this embodiment, the plant material preferably is compressed at temperatures no greater than about 70° C., for example about 45° C. To further recover arabinogalactan from the first pressed plant fiber product, the first plant fiber product may be impregnated, for example in an impregnator, with an aqueous solvent to recover an extract liquor and impregnated plant fiber, and arabinogalactan may be recovered from the extract liquor. The impregnated plant fiber product then may be compressed to recover a liquid pressate and a second pressed wood fiber product, and additional arabinogalactan may be recovered from the pressate.

Solvents

The starting plant material optionally may be combined with a solvent prior to the initial compression step. Solvents which can be added to the starting plant material prior to compression, or which can be used to impregnate the first compressed plant fiber product include water; hydrocarbons such as hexane; alcohols, such as $C_{1-10}$ aliphatic alcohols; ketones, such as $C_{1-10}$ ketones; esters; and organic acids, as well as mixtures thereof. The solvents additionally may include additives such as an inorganic compound or a surfactant. The solvents used may be, for example, an acidic or a basic aqueous solution. Organic solvents can be used which are partially, fully, or substantially non-miscible with water. Exemplary organic solvents which can be used include dimethylsulfoxide (DMSO). As defined herein, the term "solvent" includes any liquids, or gases, including organic solvents, water and aqueous solutions, in which a phytochemical is soluble which can be used to extract a phytochemical. The temperature of the solvent also may be adjusted to maximize recovery of a preselected phytochemical.

In the process for recovering arabinogalactan from Larch wood, for example, an alkaline aqueous solvent may be used in the impregnator, and the temperature of the aqueous solvent can range between about 15° C. and 100° C. As defined herein, an "aqueous solvent" includes water or buffered aqueous solutions which have been adjusted to, for example, pH 7–12. In this embodiment, the solute content of the extract can include about 1% to 90% arabinogalactan and about 1% to 10% phenols. A typical recovery from this process is an exudate including about 5% to 35% arabinogalactan, an extract including about 1% to 20% arabinogalactan, and a pressate including about 1% to 20% arabinogalactan. Additionally, the second pressed fiber product recovered from larch wood may be extracted with a solvent to recover polyphenols such as taxifolin. For this application, useful solvents include: alcohols, such as $C_{1-3}$ aliphatic alcohols; ketones such as $C_{3-6}$ ketones; ethers, such as $C_{2-6}$ ethers; and esters, such as $C_{2-6}$ esters.

At each step of processing, the isolated fractions, such as the exudate, the extract liquor, the liquid pressate, and the second pressed fiber product may be further refined to recover an isolated phytochemical, such as arabinogalactan or phenols, using methods available in the art such as chromatography, centrifuge, extraction, filtration or settling.

Exemplary Apparatus

Apparatus for pressing wood particles to recover organic compounds from wood and to produce a wood fiber product are provided, wherein the apparatus in one embodiment includes: a first plug screw feeder extractor comprising a housing having an inlet, an outlet, and regularly spaced apertures located between the inlet and outlet of the housing; a collection hood encompassing the portion of the first plug screw feeder extractor housing which contains the apertures; an impregnator having an inlet connected to the first plug screw feeder extractor outlet, an outlet, a bottom, and a valved liquor outlet means at the bottom; a second plug screw feeder extractor comprising a housing having an inlet connected to the impregnator outlet, an outlet, and regularly spaced apertures located between the inlet and outlet of the housing; a second collection hood encompassing the portion of the second plug screw feeder extractor housing which contains the apertures; and a wood particle conveyor having an inlet, a first outlet connected to the first plug screw feeder extractor inlet, and a second outlet connected to the second plug screw feeder extractor inlet, wherein the first and second outlets each contain a gate for controlling the flow of wood particles into the respective plug screw feeder extractors.

In one embodiment, fibrous plant materials, such as wood particles, are processed using system 10, illustrated in FIG. 1. The materials obtained in the process also may be further processed using methods available in the art to obtain desired organic compounds. In system 10, in FIG. 1, as described below, there are at least three sites in the system for removing the organic fluids. For ease of explanation, the recovered materials will be referred by the following different names, which will be further explained in the following description of the system 10: exudate 66, extract 113 and pressate 140.

A. Initial Processing

As described above, the fibrous plant material may come from different sources depending on the desired phytochemical to be recovered. In one embodiment, the fibrous plant material is wood, which optionally may be sized to a preferred dimension. The size of each wood particle processed will depend on the size of the equipment. Larger equipment, i.e., equipment with larger bins, throats, conveyors, etc., will have the capacity to handle larger particle sizes. In addition to solid wood particles, the runoff or liquid drain-off from other wood fibering operations may be the starting material for recovery of the selected organic chemicals.

For purposes of describing the system 10, the referenced fibrous plant material is wood 12 from the Larch tree. In a typical system 10, the wood 12 must be cut, debarked and ground or chipped in the stage 14 by a machine known in the art to comminute raw wood into wood particles 15. The raw wood particles 15 are then fed to an inlet hopper 16 for storage until the wood particles 15 are required for the next step.

When the prepared wood particles 15 are ready to be processed, they are transported from the inlet hopper 16 to a screening bin 18 by means of an inlet conveyor 20. Screening bins 18 are known to the art for separating particulate material, in this case the wood particles 15, based on size. The purpose of the screening bin 18 is to pass only those wood particles 15 having a desired size for the subsequent operation onto the next step. The screening bin 18 preferably contains first and second screens 22 and 24 with openings sized to respectively correspond to the maximum and minimum sized wood particles 15 which are preferred in the process. Raw wood particles 15 which are too large to pass through the first screen 18 are diverted by conduit 26 to a secondary chipper or grinding mill 28, known to the art for further reducing the size of wood particles 15 and recycling the properly-sized raw wood particles 15 back through the screening bin 18 via a return conduit 30.

Wood fines 32, for example wood flour or other smaller-sized particles entrapped with the wood particles 15, can be removed from the lower portion 34 of the screening bin 18 via conduit 36 and discarded or used in other applications. Alternatively, the wood fines 32 may be passed along with the properly-sized wood particles 15 to the next step for recovery of the organic compounds. If the wood fines 32 are further processed, any residual particulate material may be removed from the processed organic compounds by methods known to the art, such as air flotation or screening. The raw wood particles 15, which are small enough to pass through the first screen 22, but too large to pass through the second screen 24, are properly sized for use in the remaining steps.

For recovery of arabinogalactan from Larch trees, unlike the prior art methods, the wood particles are not required to be finely divided or defibrated in preparation for subsequent processing. The preferred size of the Larch wood particles depends upon the type of equipment used to process the wood particles. Typically, the wood particles are sized to be larger than approximately one inch in diameter and smaller than approximately four inches in diameter. The openings in the first and second screens 22 and 24 are preferably sized to conform with the necessities of the next steps in the process.

The properly sized and ground wood particles 15 are passed via a chute 38 to a storage bin 40. Storage bins 40 are well known in the art, and typically include an inlet 42 and an outlet 44, level detectors 46 for level control, and a steam 48 pretreatment inlet for optionally steaming the wood particles 15. The steam 48 pretreatment is used to heat and thaw or soften the wood particles 15 so that the energy required to compress the wood particles 15 in later processing steps is decreased. The steam 48 pretreatment inlet may add a small amount of moisture to the wood particles 15, which is beneficial if the wood particles 15 are especially dry. The storage bin 40 may also utilize vibrators (not shown) to facilitate discharge from the storage bin 40. Alternatively, a wood particle conveyor 50 positioned at the end of outlet 44 may be used to facilitate discharge of the wood particles 15 from the storage bin 40. Any conveyor known in the art, such as an auger-type conveyor including a rotating auger 52, may be suitable. It will be apparent from a further description of the system 10 that the wood particle conveyor 50 is employed for other tasks.

B. First Pressing Station

In one embodiment, referred to herein as the "Single-Stage Embodiment," the wood particles are processed in a single-stage system. Upon passing the wood particles 15 to the next step, the wood particles 15 are released from the storage bin 40 and guided by a chute 54 to the first pressing station 60, where the wood particles 15 are compressed or squeezed to express the liquid, termed the "exudate" 66, from the wood particles 15. As used herein, the exudate 66 is the organic liquid recovered from the first pressing station 60. Any suitable pressing apparatus may be employed in the first pressing station 60, including pressure rollers, cylinder presses, screw presses, and other pressing mechanisms known to the art. Both compressive and shear forces may be used on the sized wood particles. In a preferred embodiment, a screw-type press 60 is used for pressing.

Optionally, depending on the organic compound being isolated, during the pressing, the fibrous material can be combined with an additive such as solvents as described above. In contrast to prior art methods, the pressing of FPM such as Larch wood particles optionally may be accomplished in the substantial absence, and preferably in the total absence, of any added aqueous solvent to the wood particles 15, such that the wood particles 15 are near their ambient moisture content before they are compressed. This is because the steam 48 pretreatment primarily heats the wood particles 15 and does little to raise their ambient moisture content. Further, if the steam 48 pretreatment step is skipped or if alternate forms of heat pretreatment are used in the storage bin 40, the wood particles 15 will be at precisely their ambient moisture content. Since the natural or ambient moisture within the wood particle 15 is the primary solvent used to recover the exudate 66, with substantially no previous addition of any aqueous solvents, the exudate 66 is a uniquely acquired "natural" fluid. Because the exudate 66 is derived almost completely from the ambient moisture of the wood particles 15, with virtually no contamination or dilution from aqueous solvents, the exudate 66 is referred to herein as a "pure normal" exudate. This pure normal exudate 66 is a library of useful, complex concentration of the organics recovered from the wood particles 15.

The elimination of solvent addition has other advantages as well. When the wood particles 15 are compressed in an apparatus which compresses the wood particles 15 without the addition of any solvent to the wood particles 15, a greater amount of friction, shear force and compressive force may be effected on the wood particles 15, resulting in a larger amount of exudate 66 being expressed, and in an improved wood fiber product 68. As solvent is added to the wood particles 15 such that the moisture content of the wood particles 15 exceeds ambient moisture content on a dry wood basis, the extraction efficiency decreases.

In a preferred embodiment, illustrated in FIG. 1, of the first pressing station 60, the pressing station includes a plug screw feeder extractor 64. The wood particles 15 are gravity fed from the outlet 44 of the storage bin 40 through a chute 54 into a plug screw feeder extractor 64, wherein the wood particles 15 are compressed to thereby express the pure normal exudate 66. The wood particles 15, following pressing, also produce a wood fiber product 68 with unique properties.

The plug screw feeder extractor 64 is a plug screw feeder of the general type known to the art which has been modified to allow for collection and subsequent further processing of the exudate 66. The plug screw feeder extractor 64 includes a housing 70, a helical auger 72 contained within the housing 70, a high-torque, low-speed rotational driving means 74 attached to a first end 76 of the helical auger 72, and a pneumatic back-pressure damper 78. The housing 70 has an inlet 80 on its first end 76 to receive the sized wood particles 15 and an outlet 82 on its second end 84 to discharge the wood fiber product 68. The housing 70 is of circular cross-sectional shape and includes a throat 85 in which the cross-section is tapered to a narrower diameter at the second end 84 relative to the first end 76 of the housing 70. The housing 70 also has regularly spaced apertures 86 located along the throat 84 through which the exudate 66 may be expressed. The apertures 86 are sized to freely pass the exudate 66 from the housing 70 while retaining the wood fiber product 68 within the housing 70.

The helical auger 72 has a first end 76 and a second end 90, and is tapered to a narrower diameter at its second end 90 such that the degree of taper of the helical auger 72 is consistent with the degree of taper of the housing's throat 84. The auger is constructed as a casting, containing pockets between the flights of increasingly smaller volumes towards the end of the auger. The rotational driving means 74 is typically an industrial speed reducer and motor and is used to rotate the helical auger 72 relative to the housing 70. The back-pressure damper 78 is used to regulate the amount of pressure within the plug screw feeder extractor 64, and hence, the amount of squeezing to which the wood particles 15 are subjected. Pressurized air (not shown) is added to the back-pressure damper 78 for pressure control. During normal operation, the throughput of the plug screw feeder extractor 64 is mainly determined by the speed of the rotational driving means 74, and secondarily by the air pressure within the back pressure damper 78.

The pure normal exudate 66 expressed from the plug screw feeder extractor 64 is collected in a collection hood 92, which is attached to the plug screw feeder extractor 64 and which encompasses the throat 84 portion of the housing 70, including each of the apertures 86 from which exudate 66 is expressed. The bottom portion 94 of the collection hood 92 is tapered, and includes an outlet 96 for discharging the exudate 66.

The discharged pure normal exudate 66 may be subsequently screened to remove any exudate-solids 100 from a screened exudate 66A. Screens known to the art, such as a wedgewire screen 98, are suitable for this operation. The preferred mesh size for the wedgewire screen 98 for screening the exudate 66 is approximately 50 mesh. The screened pure normal exudate 66A may be refined by methods known to the art to obtain a refined organic compound product. For purifying an exudate from Larch wood particles containing arabinogalactan, many methods are known to the art, including the methods taught in by Herrick et al. and Adams et al. (supra). Other organic compounds, e.g., maltol, taxol, polyphenols, quercitin, etc. may also be extracted by these methods and others known to the art.

The wood fiber product 68 is discharged from the plug screw feeder extractor 64. The wood fiber product 68 is suitable for use in various subsequent applications, with the preferred use dependent upon the type of tree processed and the particular process parameters. When wood particles of Western Larch and Tamarack trees are used, the wood fiber product 68 obtained is a low-density-fibrous wood product which has unique and desirable characteristics. When other types of trees are used, the resulting wood fiber product 68 is suitable for use in pulping operations and any other applications known in the art to use wood fiber. In the first stage of operation, the pure normal exudate 66 and the wood fiber product 68 thus are obtained.

C. Impregnator

Reference is also made to FIG. 1 for another embodiment, in which the wood particles 68 resulting from the first stage may be processed in a two-stage system according to the following method. As described previously, the wood particles 15 are first compressed, optionally without the addition of any solvent, to express a pure normal exudate 66 and to produce a wood fiber product 68. In this embodiment, the wood fiber product 68 is then impregnated with a solvent by, for example, hydrating the wood fiber product 68 with either steam or an aqueous solvent in an impregnator 110. More specifically, with reference to FIG. 1, the wood fiber product 68 is discharged from the plug screw feeder extractor 64. The resulting wood fiber product 68 is then fed into the impregnator 110 to form a combination of impregnator liquor 112 and impregnated wood fiber 68A.

The impregnator 110 may be of the general type known to the art (e.g., the PREX™ impregnator made by Sunds Defibrator Inc., Norcross, Ga.). It includes liquid level control equipment 111 for maintaining the liquid within the impregnator 110 at a steady level by adding water, and it also includes equipment for collection and subsequent further processing of the impregnator liquor 112. The modified impregnator 110 includes a vessel 114 with an inlet 116 at a first end 118 and an outlet 120 at an opposing second end 122; two helical augers 124 inside the cylindrical vessel 114 and spanning from the first end 118 to the second end 122, the axis 126 of the augers 124 being parallel to each other; an industrial gear reducer and motor 128 for driving each of the augers 124; valved inlets 130 for admitting liquid solvents, chemicals or steam 132 into the cylindrical vessel 114; and valved impregnator liquor outlets 133 located at the first end 118 of the cylindrical vessel 114. The motor 128 can be variable speed to permit the amount of time the chips spend in the impregnator fluid to be varied.

A variety of alternatives exist with respect to impregnating the wood fiber product 68 in the impregnator 110. The impregnating may comprise rehydrating the wood fiber product 68 with the exudate 66, a pressate 140 expressed from a second plug screw feeder extractor 64A, with steam 132, or preferably, with an aqueous or other solvent to resaturate the wood fiber product 68. The steam 132 or aqueous solvent used in the impregnator 110 may be at a variety of pH levels and temperatures, to result in a variety of compositions of the impregnator liquor 112.

In one mode, water can be introduced through inlet 130 at a high temperature, typically around 90° C. Generally, a solution of a chemical additive such as an alkali (0.1M sodium hydroxide) is added. This process will yield different compounds when different wood fiber products 68 are input. For example, if the wood fiber product is from a species of the Larix genus, this process will recover arabinogalactan and phenols. Phenols including polyphenols have utility in a variety of functions, for example, as animal feed additives.

In contrast, hydrating the wood fiber product 68 with cold water (at a temperature no greater than about 70° C., e.g., about 45° C.) will yield a product with different chemical content. If the wood is from the Larix genus, the impregnator liquor 112 product will yield purer arabinogalactan because the phenols will largely remain in the wood fiber product 68.

The wood fiber product 68 is introduced into the impregnator 110 at a point under the liquid level of the impregnator liquor 112 by the plug screw feeder extractor 64. The wood fiber product 68 is then carried up the impregnator 110 via the twin counter-rotating augers 124 and through the impregnator liquor 112. While the wood fiber product 68 is in a compressed state when it first leaves the plug screw feeder extractor 64 and enters the impregnator liquor 112, it rapidly absorbs the impregnator liquor 112 until it reaches a moisture content which is at least equal to the moisture content of the wood particles 15 when they first entered the system 10. The impregnator liquor 112 dissolves much of the remaining organic chemicals within the wood fiber product 68, e.g., arabinogalactan, which were not released during the pressing step at the first pressing station 60. The chemicals will mix with the impregnator liquor 112 and form a chemical "extract" 113 which may then be recovered from the impregnator 110.

If the impregnation is performed with the exudate 66 as the rehydration medium, the extract 113 will have contents virtually indistinguishable from those of the pure normal exudate 66. This is because no aqueous solvents have yet been added to the wood fiber product 68. On the other hand, if the impregnator 110 rehydration medium is steam or an aqueous solvent, the extract 113 will not have pure normal content. The extract 113 will be tainted with solvent and will therefore generally require extra processing to separate it into its pure organic chemical components. The pressate 140 may also be used as the rehydration medium.

The extract 113 may be continuously collected from the impregnator 110 by means of the valved impregnator liquor outlet 133 at the first end 118 of the impregnator vessel 114 in either a continuous or batchwise manner. As with the exudate 66 from the plug screw feeder extractor 64, the extract 113 may be subsequently screened to remove any impregnator-solids 134, and may also be refined by methods known to the art to obtain a refined organic product, e.g., arabinogalactan. The extract 113 may also be combined with the exudate 66 from the plug screw feeder extractor 64.

The impregnated wood fiber 68A is discharged from the impregnator 110 via the outlet 120. An outlet chute 121 then feeds the impregnated wood fiber 68A to an impregnator conveyor 138, which in turn feeds the impregnated wood fiber 68A into a drop chute 136. The impregnated wood fiber 68A optionally is gravity fed through the drop chute 136 into a second pressing station 60A.

D. Second Pressing Station

The second pressing station 60A preferably includes a second plug screw feeder extractor 64A, which performs essentially the same function as the plug screw feeder extractor 64. In the second plug screw feeder extractor 64A, the impregnated wood fiber 68A is compressed in a manner similar to the compressing of the wood fiber product 68 at the first plug screw feeder extractor 64. The impregnated wood fiber 68A thereby expresses a more finely divided second wood fiber product 142 and also a "pressate" 140.

Because the pressing in the second plug screw feeder extractor 64A will express the impregnator liquor 112 which was retained within the impregnated wood fiber 68A, it can be appreciated that the pressate 140, like the extract 113, will also have compositions which vary depending on the types and parameters of the solvents used in the impregnator 110. For example, if the rehydration medium added to the impregnator 110 is the pure normal exudate 66, the pressate 140 will have pure normal content as well. On the other hand, if an aqueous solvent is used as the rehydration medium in the impregnator 110, the pressate will not be in pure normal form.

The pressate 140 is collected in a second collection hood 94A. The second collection hood 94A is essentially the same as the first collection hood 92. The pressate 140 may be further processed as described with respect to the exudate 66 from the plug screw feeder extractor 64 so that desired organic compounds may be refined from the pressate 140.

The recompressed second wood fiber product 142 is discharged from the second plug screw feeder extractor 64A through tee pipe 182, attached to pneumatic cylinder 184, and discharge conveyer 138B as a second wood fiber product 142. The second wood fiber product 142 may be used in the same or similar applications as described above with respect to the wood fiber product 68. Because the second plug screw feeder extractor further divides the impregnated wood fiber product 68A, the second wood fiber product 142 has fibers of even lower density than those of the wood fiber product 68. Chip disintegration in the second plug screw feeder extractor 64A may not be as great as that in the first plug screw feeder extractor 64.

E. Bypass Embodiment

In a further process embodiment, the properly sized wood particles 15 may be processed in two single-stage systems run in parallel to each other according to the following method. This method is similar to the two-stage system, but the impregnation step is bypassed. The wood particles 15 are fed to the storage bin 40. The wood particles 15 are then simultaneously fed to the first pressing station 60 and the second pressing station 60A by means of the wood particle conveyor 50. Accordingly, the wood particle conveyor 50 includes a particle conveyor inlet 150 suitable for the wood particles 15, a first outlet 152, a second outlet 154, and a rotating auger 52 or similar transport means for moving the wood particles 15 from the particle conveyor inlet 150 to either or both of the first and second outlets 152 and 154. The first and second outlets 152 and 154 each contain a gate 158 and 160 respectively for controlling the flow of the wood particles 15 out of the wood particle conveyor 50.

The wood particles 15 are then processed as described with respect to the single-stage system embodiment. Because the impregnating step carried out in the impregnator 110 is essentially bypassed, i.e., the impregnator is used only as a transport element, the pressing in the second plug screw feeder extractor 64A is accomplished without the addition of any aqueous solvent to the wood particles 15 in a manner similar to the pressing in the plug screw feeder extractor 64. The dry impregnator 110 conveys the wood chips to the conveyer 138, through gate 180 and chute 38A to conveyer 138A, through chute 38B to tee pipe 182. Thus, a second pure normal exudate is expressed (at the same location as the pressate 140 of the previous embodiment), and a second wood fiber product 142 is produced as well. This bypass embodiment may be a preferred embodiment when greater production of pure normal exudate and/or wood fiber product 68 and 142 is desired.

The apparatus and processes, as detailed above, permit extreme flexibility with respect to the type of products resulting from processing the wood particles 15. The processes may be used to manufacture at least five products: pure normal exudate 66, wood fiber product 68, extract 113, pressate 140, and second wood fiber product 142, each of which may be further refined to produce a purified phytochemical. Thus, even for a single type of plant material, the apparatus and process may be employed to simultaneously produce a variety of different products. The various process conditions, including choice of plant material, solvents, temperature and process steps, can be designed to optimize the production of different effluent compositions.

Advantages

The apparatus and process may be used and optimized to produce a variety of different products simultaneously, from a wide variety of different fibrous plants. The various process conditions can be designed to produce various combinations of product effluent compositions. In one embodiment, the efficiency of recovery of arabinogalactan from Larix wood particles is significantly higher than that obtainable using prior art methods. Significantly fewer resources are required to obtain an arabinogalactan exudate which has a significantly higher concentration of arabinogalactan than prior art exudates, because the wood is not required to be finely ground prior to processing, less process solvent is required to effect the recovery, and during refinement of the resulting exudate, less water need be removed to obtain a dry arabinogalactan or a very high concentration arabinogalactan solution. This increased efficiency results in decreased operating costs. The process may also be used to isolate many other desirable plant metabolites, such as phenols (separately, or in combination with arabinogalactan), such as quercitin, taxol, and maltol, and further may be used to isolate and identify new metabolites in different plant species.

Additionally, a low density fibrous wood fiber product may be obtained with enhanced purity and improved characteristics. For example, a higher ratio of fiber to non-fiber components in the resulting fibrous wood product may be obtained from Larch wood, since more arabinogalactan is removed from the remaining fiber. The low-density-fibrous wood product obtained from Larch wood is broken down and no longer in chip-recognizable form, and thus is suitable, for example, in applications including: pulping operations; pelletizing for use as a domestic and industrial fuel; as a dietary fiber additive as for use in animal feed; mulch; fiberboard production; preparation of cellulose; and as a liquid absorbent for oil.

The present invention will be further understood by reference to the following non-limiting examples.

Example 1: Isolation of Arabinogalactan from Larch Wood

Air-dry chips of Western Larch (*Larix occidentalis*) (43.8 kg, 26.7 kg dry weight) were passed through a plug screw feeder extractor to yield 6.6 kg of liquid exudate and a first pressed plant fiber product. A sample of the exudate was centrifuged and freeze-dried and shown to contain 35% (w/w) of total dissolved solids. The dried solids were pale beige in color and contained 93% of high molecular weight arabinogalactan. This corresponds to a yield of 7.1% of relatively pure arabinogalactan, based on the dry weight of wood. In comparison, Stractan 10 obtained by countercurrent hot water extraction of Western Larch contains about 88% of high molecular weight arabinogalactan and is highly colored.

The first pressed plant fiber product was extracted with water at room temperature and then passed through a second plug screw feeder extractor to recover a liquid pressate and a second pressed plant fiber product. The liquid pressate from the second press contained 8.9% total dissolved solids and the high molecular weight AG in the solids corresponded to 8.2% yield based on original dry wood.

In another run, the first pressed plant fiber product were extracted with water at 80°–90° C. and then passed through a second plug screw feeder extractor, manufactured by Sunds Defibrator Inc., Norcross, Ga., to recover a liquid pressate and a second pressed plant fiber product. The pressate from the second press contained 7% total dissolved solids, which, after drying, included 88% high molecular weight arabinogalactan and about 10% phenols.

The second pressed plant fiber product is a low density dry fiber product. Further extraction of the second pressed plant fiber product with water at room temperature (without further pressing) yielded an additional 9.8% of high molecular weight AG based on the original dry wood, and a purified water extracted fiber product suitable for further use.

Example 2: Isolation of Taxifolin from Larch Wood

The second pressed plant fiber product from example 1, (or the purified water extracted fiber product) was extracted with methanol at room temperature. Evaporation of the methanol extract yielded a pale yellow amorphous solid corresponding to 4.8% of the dry weight of the final fiber, which included primarily phenols. Analysis of the phenols by proton magnetic resonance (using furfural as added internal standard), or by liquid chromatography (using authentic taxifolin as external standard), showed that 71% of the phenols were taxifolin. Pure taxifolin can be isolated from this product by preparative liquid chromatography.

Modifications and variations of the present invention will be obvious to those skilled in the art from the foregoing detailed description. Such modifications and variations are intended to come within the scope of the following claims.

What is claimed is:

1. A method of recovering an exudate comprising arabinogalactan, a pressed plant fiber product, and an extract liquor from a fibrous woody plant material, the method comprising
    a) compressing the fibrous woody plant material in absence of any added solvent to recover a liquid exudate comprising arabinogalactan from the fibrous woody plant material and a first pressed plant fiber product from the fibrous woody plant material; and
    b) impregnating the first plant fiber product with a solvent to recover an extract liquor and impregnated plant fiber.

2. The method of claim 1 wherein the fibrous woody plant material is from a tree selected from the group consisting of larch, hemlock, black spruce, douglas fir, cedar, juniper and maple.

3. The method of claim 1 wherein the fibrous plant material is compressed in a plug screw feeder extractor.

4. The method of claim 1 wherein the first plant fiber product is impregnated in an impregnator.

5. The method of claim 1 further comprising recovering a phytochemical from at least one of the exudate, the extract liquor or the impregnated plant fiber product.

6. The method of claim 1 further comprising compressing the impregnated plant fiber to recover a liquid pressate and a second pressed fiber product.

7. The method of claim 1 wherein the solvent comprises at least one material selected from the group consisting of water, hydrocarbons, alcohols, ketones, esters and acids.

8. The method of claim 1 wherein the solvent comprises a material selected from the group consisting of an inorganic compound and a surfactant.

9. The method of claim 1 wherein the solvent is selected from the group consisting of an acidic and a basic aqueous solution.

10. The method of claim 1 wherein the solvent is selected from the group consisting of organic solvents which are substantially non-miscible with water, organic solvents which are partially miscible with water and organic solvents which are highly miscible with water.

11. The method of claim 1 wherein the fibrous plant material comprises wood or bark of a plant of the genus Larix.

12. The method of claim 11 wherein the plant material is compressed under temperatures no greater than 70° C.

13. The method of claim 11 wherein the fibrous plant material has an ambient moisture content.

14. The method of claim 11 wherein step b) comprises impregnating the first plant fiber product with an aqueous solvent to recover an extract liquor and impregnated plant fiber; and wherein the method further comprises:
    i) recovering arabinogalactan from the extract liquor;
    ii) compressing the impregnated plant fiber product to recover a liquid pressate and a second pressed wood fiber product, and recovering arabinogalactan from the liquid pressate.

15. The method of claim 14 wherein the solute component of the extract liquor comprises about 1% to 90% arabinogalactan and about 1% to 10% phenols.

16. The method of claim 14 wherein the liquid exudate comprises about 5% to 35% arabinogalactan, the extract liquor comprises about 1% to 20% arabinogalactan, and the liquid pressate comprises about 1% to 20% arabinogalactan.

17. The method of claim 14 wherein the second pressed wood fiber product is a low density fibrous wood product.

18. The method of claim 14 wherein the aqueous solvent is alkaline.

19. The method of claim 18 wherein the temperature of the aqueous solvent is between about 15° C. and 100° C.

20. The method of claim 14 further comprising recovering a phytochemical from at least one of the liquid exudate, the liquid pressate, and the second pressed wood fiber product.

21. The method of claim 20 wherein the phytochemical is selected from the group consisting of arabinogalactan and a phenol.

22. The method of claim 14 further comprising extracting the second pressed fiber product with an extraction solvent to recover a phenol.

23. The method of claim 22 wherein the extraction solvent is selected from the group consisting of alcohols, ketones, ethers and esters.

24. The method of claim 22 wherein the phenol is taxifolin.

* * * * *